(12) United States Patent
Curcio

(10) Patent No.: US 7,820,023 B2
(45) Date of Patent: Oct. 26, 2010

(54) PRECONCENTRATION INTERFACE COUPLING LIQUID CHROMATOGRAPHY TO CAPILLARY ELECTROPHORESIS

(75) Inventor: Mario Curcio, Sins (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1209 days.

(21) Appl. No.: 11/169,103

(22) Filed: Jun. 28, 2005

(65) Prior Publication Data

US 2006/0086611 A1    Apr. 27, 2006

(30) Foreign Application Priority Data

Jul. 3, 2004    (EP)    .................................. 04015701

(51) Int. Cl.
*G01N 27/447*    (2006.01)
*G01N 30/02*    (2006.01)
(52) U.S. Cl. ................. 204/451; 204/453; 204/601; 204/604; 422/70
(58) Field of Classification Search ......... 204/601–605, 204/451–455; 422/70; 251/281
See application file for complete search history.

(56) References Cited

U.S. PATENT DOCUMENTS

| | | |
|---|---|---|
| 3,735,640 A | 5/1973 | Chizhov et al. |
| 4,043,678 A | 8/1977 | Farrell et al. |
| 5,087,338 A * | 2/1992 | Perry et al. ............... 435/173.2 |
| 5,240,577 A * | 8/1993 | Jorgenson et al. ........... 210/656 |
| 5,599,503 A | 2/1997 | Manz et al. |
| 6,387,234 B1 * | 5/2002 | Yeung et al. ................ 204/451 |
| 6,558,523 B1 * | 5/2003 | Swierkowski ............... 204/604 |
| 2002/0119482 A1 * | 8/2002 | Nelson et al. .................. 435/6 |
| 2002/0121444 A1 | 9/2002 | Devoe et al. |

(Continued)

FOREIGN PATENT DOCUMENTS

EP    1 279 953 A2    1/2003

(Continued)

OTHER PUBLICATIONS

Gottschlich, N. et al., "Two-Dimensional Electrochromatography/Capillary Electrophoresis on a Microchip", Analytical Chemistry, vol. 73, No. 11, Jun. 1, 2001, pp. 2669-2674.

(Continued)

*Primary Examiner*—Kaj K Olsen
(74) *Attorney, Agent, or Firm*—McDonnell Boehnen Hulbert & Berghoff LLP

(57) ABSTRACT

An arrangement for two-dimensional separation of a complex analyte mixture is provided comprising a first separation device for the separation in a first dimension and a second device for the separation in the second dimension. In the area of the interface between the first and the second device a concentration zone is arranged for concentrating the individual sample fractions or components, respectively, leaving the first device before introduction into the second device. The concentration zone is defined in a segment between two or more electrodes seen in flow direction of the sample or sample fractions to be separated. The concentration is achieved by applying a voltage between two electrodes with polarity opposite to the charge of the components of the fraction, sufficiently strong to win the dragging force of the hydrodynamic flow. The introduction into the second device is carried out by turning off the potential difference between the electrodes.

14 Claims, 1 Drawing Sheet

U.S. PATENT DOCUMENTS

| | | | |
|---|---|---|---|
| 2003/0012697 A1 | 1/2003 | Hahn et al. | |
| 2003/0168392 A1 | 9/2003 | Masuda | |

FOREIGN PATENT DOCUMENTS

| | | |
|---|---|---|
| JP | 2001296275 | 10/2001 |
| JP | 2003149218 | 12/2004 |
| JP | 2004101477 | 10/2005 |
| WO | WO 01/53794 A | 7/2001 |
| WO | WO 01/71330 A1 | 9/2001 |
| WO | WO 02/37091 A1 | 5/2002 |

OTHER PUBLICATIONS

Ivanov, R. et al., "High-efficiency peptide analysis on monolithic multimode capillary columns: Pressure-assisted capillary electrochromatography/capillary electrophoresis coupled to UV and electrospray inonization-mass spectrometry", Electrophoresis, vol. 24, Nov. 21, 2003, pp. 3663-3673.

Valcarcel, M. et al. "Coupling continuous separation techniques to capillary electrophoresis", Journal of Chromatography A, Elsevier Science, NL, vol. 924, No. 1-2, Jul. 27, 2001, pp. 3-30.

Astorga-Wells, J., Swerdlow, H. "Fluidic Preconcentrator Device for Capillary Electrophoresis of Proteins", Analytical Chemistry, vol. 75, No. 19, Oct. 1, 2003, p. 5207-5212.

Astorga-Wells et al., "A microfluidic electrocapture device in sample preparation for protein analysis by MALDI mass spectrometry", Anal. Chem., Oct. 1, 2003, 75, 5213-19.

Beranova-Giorgianni, Sarka. "Proteon analysis by two-dimensional gel electrophoresis and mass spectrometry: strengths and limitations." Trends in Anal. Chem. 2003, 22, 273-281.

Opiteck et al. Comprehensive two-dimensional high-performance liquid chromatography for the isolation of overexpressed proteins and protein mapping. Anal. Bioch. 1998, 258, 349-361.

Opiteck et al. "Comprehensive on-line LC/LC/MS of proteins". Anal. Chem. 1997, 69, 1518-1524.

Washburn et al. "Large-scale analysis of the yeast proteome by multidimensional protein identification technology." Nature Biotech. 2001, 19, 242-247.

Wolters et al. "An automated multidimensional protein identification technology for shotgun proteomics." Anal. Chem. 2001, 73, 5683-5690.

Wagner et al. "An automated on-line multidimensional HPLC system for protein and peptide mapping with integrated sample preparation." Anal. Chem. 2002, 74, 809-820.

Moore et al. "Rapid comprehensive two-dimensional separations of peptides via RPLC-optically gated capillary zone electrophoresis." Anal. Chem. 1995, 67, 3448-3455.

Lewis et al. "Comprehensive on-line RPLC-CZE-MS of peptides." J. Am. Soc. Mass Spectrom. 1997, 8, 495-500.

Han et al. "Quantitative profiling of differentiation-induced microsomal proteins using isotope-coded affinity tags and mass spectrometry." Nature Biotech. 2001, 19, 946-51.

Osbourn et al. "On-line preconcentration methods for capillary electrophoresis." Electrophoresis 2000, 21, 2768-2779.

Valcarcel et al. "Coupling continuous separation techniques to capillary electrophoresis." Journal of Chromatography A, 924 (2001) 3-30.

Issaq, et al., *A simple two-dimensional high performance liquid chromatrography/high performance capillary electrophoresis set-up for the separation of complex mixtures*, Electrophoresis 20:1533-1537 (1999).

Shen, et al., *Proteomics based on high-efficiency capillary separations*, Electrophoresis 23:3106-3124 (2002).

Gygi, et al., Quantitative analysis of complex protein mixtures using isotope-coded affinity tags, Nature Biotechnology 17:994-999 (1999).

Larmann, et al., Two-dimensional separations of peptides and proteins by comprehensive liquid chromatography-capillary electrophoresis, Electrophoresis 14:439-447 (1993).

* cited by examiner

PRECONCENTRATION INTERFACE COUPLING LIQUID CHROMATOGRAPHY TO CAPILLARY ELECTROPHORESIS

BACKGROUND OF THE INVENTION

The present invention relates to an arrangement for two-dimensional separation of a complex mixture of e.g., peptides, and methods for producing such arrangement by liquid chromatography. In particular, the invention relates to reversed phase liquid chromatography (RPLC) followed by capillary electrophoresis (CE) spraying directly into a mass spectrometer.

Two-dimensional liquid chromatographic/mass-spectrometric methods (LC/MS) start playing a key role in proteomics research and applications due to the fact that 2D LC has been found to overcome some of the limitations crucial to 2D Polyacrylamid Gel Electrophoresis (PAGE). The main advantages of this process are automation, shorter analysis time, higher sensitivity and increased reproducibility. Dilute samples can be concentrated on-column and coupling with different detection systems is possible, like UV, LIF and especially MS leading to quicker identification and quantitation.

Analysis at the peptide level is preferable for several reasons but mainly because peptides are initially more soluble in a wider variety of solvents and are easier to separate than the parent proteins. There is however a disadvantage in working with peptides, which is the increase in the number of species that have to be solved, thus demanding higher resolution during separation and making the use of available pre-fractionation techniques more important.

The basic idea of an on-line 2D-LC system is to have a slow separation in the first dimension and a fast separation in the second dimension. In order to match the requirements for high resolution in the second dimension without reducing the sampling rate or slowing down the first dimension, at least two second dimension columns need to be eluted in parallel. The most reported but also the most applied and commercialized 2D-LC approach is ion exchange chromatography (IEX) followed by RPLC. The two techniques are fully orthogonal, the first based on a charge separation mechanism (salt elution steps), the second based on hydrophobicity (gradient elution with organic solvent). IEX is not compatible with MS, thus it is employed as first dimension. Fractions from IEX are trapped and washed on one or two parallel enrichment columns, then subjected to second separation by RPLC (one or two parallel columns), which can be coupled directly to MS typically trough ESI interface. A limitation of this approach is still the overall long time of analysis.

Theoretically, one of the combinations offering most advantages is LC followed by Capillary Zone Electrophoresis (CZE) but thus far, nothing has been commercialized for this specific coupling and little can be retrieved in the literature. These two techniques are also orthogonal and compatible between them and with mass spectrometry. They both provide high resolution increasing the total peak capacity and together can be faster than any other 2D combination.

The rate at which CZE separations can be carried out allows the continuous sampling of the effluent from the first column into the second, completing the 2D analysis in the time it takes to complete the first dimension, that is the time it takes to perform an RPLC separation. The critical issue that has historically slowed the development of this strategy is probably the interface between the two separation techniques. Interesting ideas, not always intended for this specific coupling, are more or less valid solutions. A few alternative methods are described in the prior art, like that based on a mechanical valve and those based on a flow gating or optical gating concept. Another concept could also be employed based on dispensing, by one of several means, droplets of defined volumes from a continuous flow into for example a capillary for CE. Other concepts, e.g., based on control of EOF (Electro Osmotic Flow) are described in the prior art. But in all cases, besides individual limitations, a common disadvantage still remains, that is most of the effluent is sent to waste with risk to lose information and sensitivity is certainly not improved.

On-column preconcentration in capillary electrophoresis is known in the art, however, these known methods require either discontinuous buffer systems, e.g., for isotachophoresis and field amplification, or the use of adsorbing or binding materials generally also requiring a change in the mobile phase or buffer for desorption. Electrokinetic trapping has also been reported in the prior art, where proteins are trapped on silica particles under an applied electric field and eluted by pressure in absence of electric field. A fluidic electrocapture device based on the equilibrium between hydrodynamic and electrical forces has also been described. However, this was meant for one-step sample cleanup of peptides and proteins before e.g., Matrix Assisted Laser Desorption/Ionization-Mass Spectrometry (MALDI-MS) or preconcentration before one-dimensional off-line analysis by capillary electrophoresis, and in fact, it only helps to prove the principle on which the interface of this invention is based

SUMMARY OF THE INVENTION

It is against the above background that the present invention provides certain unobvious advantages and advancements over the prior art. In particular, the inventor has recognized a need for improvements in preconcentration interface coupling liquid chromatography to capillary electrophoresis.

Although the present invention is not limited to specific advantages or functionality, it is noted that the present invention provides a solution to overcome the limitation at the interface stage between the first separation and the following separation step without the disadvantages reported in relation to the proposed ideas. More particularly, the present invention provides an interface between the RPLC separation and the following CE separation.

In accordance with one embodiment of the present invention, an arrangement for two-dimensional separation of a complex analyte mixture is provided comprising a first separation device for the separation in a first dimension and a second device for the separation in the second dimension with an area of interface between the first and the second device, further comprising a concentration zone for concentrating the individual sample fractions or components, respectively, leaving the first device before introduction into the second device.

In accordance with another embodiment of the present invention, a method for two-dimensional liquid chromatography/electrophoresis/mass spectrometry is provided comprising separating a sample mixture in a reversed phase liquid chromatography followed by a capillary zone electrophoresis, wherein in the area of the interface between the reversed phase liquid chromatography and the capillary zone electrophoresis the fractions leaving the reversed phase liquid chromatography are concentrated before insertion into the following capillary zone electrophoresis.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

In accordance with an embodiment of the present invention, a method is provided for sampling the effluent of the first column into the second so that sufficient time is given for Capillary Zone Electrophoresis separation of an injected fraction without contamination from the continuous flow. Fractions eluting from the first column are concentrated in one short segment, defined by two electrodes, before the next injection between a second separation and another one. This not only results in the conservation of all the information contained in the first-dimension separation but also in a much increased sensitivity and resolution in the second dimension.

In accordance with another embodiment of the present invention, the flow is never stopped but held constant at the rate at which the first separation, such as e.g., RPLC, is run (e.g., 100 nl/min) regardless of EOF value during the second step separation, such as e.g., the CE, or pressure drops within the system, for whatever reason, e.g., clogging or bubbles. This can be made possible thanks to recent advances in nano-pump technology commercialized, e.g., by Agilent Technologies and Dionex LC Packings. An effect of this is that a stable electrospray for MS-analysis can also be assured.

Therefore, in one embodiment, the present invention refers to the combination of nano-RPLC instead of micro-RPLC with CZE. Micro-RPLC is usually based on columns with an inner diameter in the range of about 0.3 to about 3 mm and having typical flow rates in the range of about 1 to about 500 µl/min, while nano-RPLC is based on columns with an inner diameter in the range of about 75 to about 100 micron and typical flow rates of about 0.1 to about 1 µl/min (about 100 to about 1000 nl/min). As a consequence, the flow rates applied for LC (<about 200 nl/min) are compatible with the separation speed of CZE which is now perfectly on line with the first column and in turn is coupled to MS via an ESI interface. In other words, all the effluent from RPLC flows straight through the CZE channel without valves or dead volumes, nothing is sent to waste and no dilution occurs.

Figure 1A:
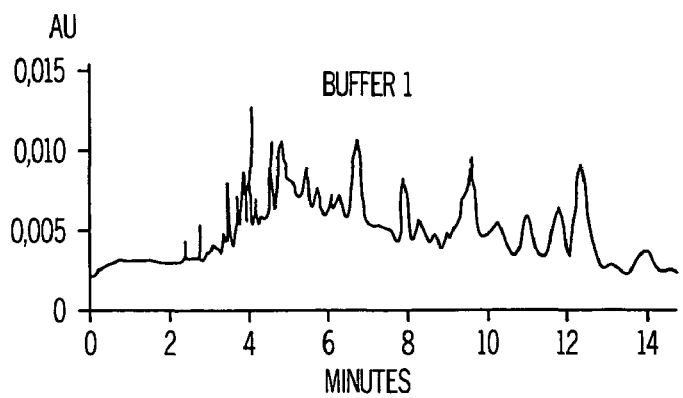
FIG. 1a is a reference electropherogram for a chosen sample obtained by a capillary electrophoresis method using an electrolyte buffer under conditions that are incompatible with a first dimension chromatographic step and with mass spectrometry detection in accordance with one embodiment of the present invention.
Figure 1B:
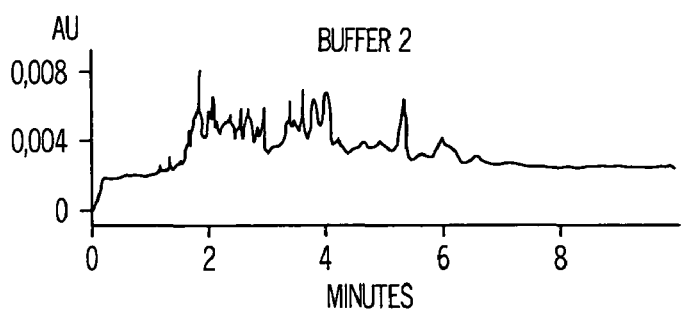
FIG. 1b is a reference electropherogram for a chosen sample obtained by another capillary electrophoresis method using an electrolyte buffer under conditions that are also incompatible with a first dimension chromatographic step and with mass spectrometry detection in accordance with one embodiment of the present invention.
Figure 1C:
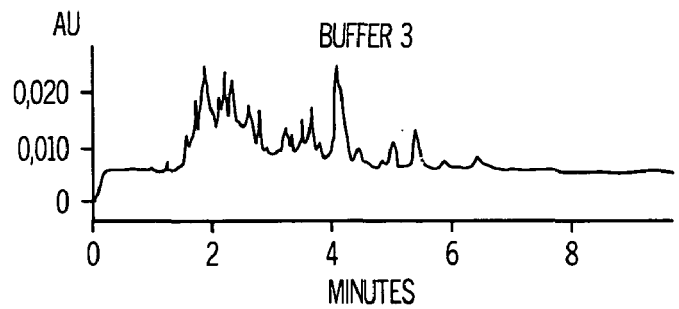
FIG. 1c is an electropherogram for the same chosen sample as in FIGS. 1a and 1b, showing similar resolution compared to FIGS. 1a and 1b, but obtained by using a different electrolyte buffer under conditions which, with variations still allowed, are more compatible with a first dimension chromatographic step and with mass spectrometry detection, thus allowing a continuous on-line coupling in accordance with one embodiment of the present invention.

Changing buffer before CZE analysis is not necessary as conditions can be found which are both compatible with RPLC and CZE separations and also with mass spectrometry. This was proven with some experiments where the resolution achieved by CZE for a mixture of peptides (tryptic digest of IgG yielding 30 peptides) in a buffer consisting of 20% Acetonitrile (ACN)/0.4% Triethylamine (TEA)/0.3% Trifluoroacetic acid (TFA) (FIG. 1c) was comparable with the resolution achieved in optimal well-described buffer systems incompatible with MS and RPLC due to the high salt content and the presence of additives such as urea (FIGS. 1a and 1b). Buffer 1, according to FIG. 1a, is consisting of iminodiacetic acid (IDA) 50 mM, Hydroxyethyl cellulose (HEC) 0.5% 7M urea. Buffer 2 is consisting of 50 mM IDA/10% Trifluoroethanol (TFE)/0.5% HEC. The graph according to FIG. 1c is showing a separation in second dimension that could result from the present invention.

Another possibility is also to use capillary electrochromatography (CEC) as first dimension separation.

The problem of electrolysis and bubble formation occurring when internal electrodes are used can be prevented by integrating instead salt-bridge electrodes or conductive membranes as described in Astorga-Wells et al. "A microfluidic electrocapture device in sample preparation for protein analysis by MALDI mass spectrometry. *Anal. Chem.* Oct. 1, 2003, 75, 5213-19; and Astorga-Wells et al. "Fluidic preconcentrator device for capillary electrophoresis of proteins. *Anal. Chem.* Oct. 1, 2003, 75, 5207-12. As part of this invention, two microelectrodes are used for preconcentration, consisting, according to a possible example, of microchannels in contact with the CE channel by means of a very narrow aperture in the order of e.g., about 2 to about 3 µm and filled with e.g., a Nafion® polymer or other ion selective material. Nafion® is basically Teflon® (polytetrafluoroethylene) with sulfonic acid groups interspersed within it, with a very high affinity for water. Each sulfonic acid can bind up to 13 water molecules, attracting them as water-of-hydration. Interconnections between the sulfonic acid groups lead to very rapid transfer of water through the Nafion® and thus also protons. One of the main applications of Nafion® is indeed as proton exchange membrane in polymer electrode fuel cells. Eventually, other small positive ions can pass through but not analytes of the size of a peptide. This makes possible that peptides co-eluting in a chromatographic peak can be concentrated within a short zone comprised between two of these electrodes by applying a voltage across, with polarity opposite to the charge of the peptides (positive in this case) sufficiently strong to win the dragging force of the hydrodynamic flow. Injection for CE is carried out by turning off the potential difference between the two electrodes and allowing the compacted sample plug to be transported by the flow for the time necessary to pass the second electrode and exit the concentration zone. The voltage applied for separation between second electrode and cathode is always on, while that between the two concentration-electrodes is turned off only during injection.

Figure 2:
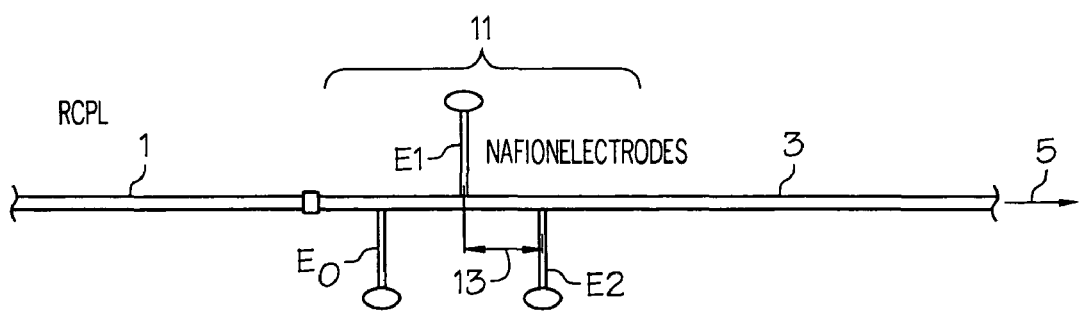
FIG. 2 is a schematic not-to-scale representation of a pre-concentration interface between first and second separation column, in line with each other, defined by the zone between at least two or more electrodes in accordance with one embodiment of the present invention.

In accordance with still another embodiment, the invention is e.g., described in further details with reference to FIG. 2, where a schematic representation of the invention is shown.

After a first separation device, such as e.g., RPLC column, the separated samples or fractions, respectively, are inserted into an intermediate zone 11 which ends into a proceeding further separation device 3, such as e.g., CE separation channel. Leaving the separation channel 3, samples are forwarded and injected or sprayed into a mass spectrometric device 5.

The intermediate zone 11 comprises two electrodes E1 and E2 which are arranged at a distance in between which a so-called preconcentration zone 13 is defined.

Fractions leaving the RPLC column 1 are first pre-concentrated in the preconcentration zone 13 by maintaining the two electrodes E1 and E2 at a potential difference in such a way, that analytes in the fractions cannot pass the electrode E2. After a certain time or a preconcentration time, respectively, the electrodes are switched off or the polarity is switched vice versa so that the preconcentrated analyte fraction can pass the electrode E2 and enter into the second separation device 3 which is e.g., a CE separation channel. By introducing a pre-preconcentration zone defined by electrodes $E_0$ and $E_1$, it is further possible to stop the entering of further components leaving the RPLC device in the preconcentration zone 13 before injection into the CE zone 3 is completed.

Of course, FIG. 2 shows only one example of a design according to the present invention. It is of course possible to arrange further electrodes to define further zones for preconcentration.

An advantage of the inventive arrangement is that the flow as such is not interrupted and the flow of any solvents or transport liquids shall remain constant. Furthermore, no effluent is sent to waste with the risk to lose information.

To give an idea of the dimensions and the values for the inventive methods, the values for flow rates, voltages and time of analysis the following calculations in the sense of an example can be made, which are intended to illustrate the invention, but not limit the scope thereof:

EXAMPLES

Example 1

For RPLC a C18 column 15 cm long×75 μm ID (inner diameter) can be used and a flow rate for gradient elution of 100 nl/mn applied. The CE channel where the RPLC effluent is flowing can be 50 μm ID and the effective length where electrophoresis occurs 5 cm. The preconcentration zone before CE separation is 1 mm long.

In this system the linear flow velocity ($v_f$) is 0.085 cm/s. The electrophoretic mobility (μ) of peptides, calculated from separations in the buffer system described above, typically range from $1.0 \times 10^4 \, cm^2 \, sec^{-1} \, V^{-1}$ to $1.6 \times 10^{-4} \, cm^2 \, sec^{-1} \, V^{-1}$. From the equation $v_e = \mu E$, where $v_e$ is the electrophoretic velocity and E the electric field, an electric field of 2 KV/cm, that is 10 KV across 5 cm, would yield a $v_e$ ranging between 0.2 cm/s and 0.36 cm/s. So the total velocity ($v_{tot}$), which is the sum of $v_f$ and $v_e$, would range between 0.285 cm/sec and 0.445 cm/sec, that is a detection time between 10 s for the first peak and 18 s for the last peak, while for a chromatographic peak an estimate of 30 s is reasonable. This means that there is plenty of time to run electrophoresis while the next chromatographic peak is concentrated before the next injection.

Heat generation and loss of resolution by Joule effect due to the high voltage is not a big issue because of the low ionic strength of the liquid system, the small dimensions of the channel and the flow rate bringing fresh liquid all the time.

The value of the trapping electric field must be greater than the ratio between $v_f$ and the lowest peptide mobility, that is greater than 850 V/cm, that is greater than 85 V across 1 mm. The time during which this electric field should be zero to allow injection is then 1.2 s.

A very high concentration factor can be achieved.

In another version of this interface the concentration zone, still 1 mm×50 μm, is filled with cation exchange material and sample stacking occurs in absence of an electric field in this zone. Sample desorption is then achieved by applying sufficient voltage with polarity in the same direction of the flow. An estimate of the electric field required is not made in this case as this depends on the final stationary phase used, however the low pH and the presence of ion pairing agents such as TFA should lower the value of this field. The above mentioned example as well as the schematic representation shown in FIG. 2 is used for further explaining the present invention which of course is not at all limited in any sense to the example and the representation as shown in FIG. 2.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An arrangement for two-dimensional separation of a complex analyte mixture comprising a first separation device comprising a liquid chromatography separation column for the separation in a first dimension and a second device comprising a capillary electrophoresis separation device for the separation in the second dimension with an area of interface between the first and the second device, further comprising a concentration zone within the area of interface for concentrating the individual sample fractions or components, respectively, leaving the first device before introduction into the second device, wherein the concentration zone is defined in a segment between two or more electrodes in a flow direction of the sample or sample fractions to be separated, and wherein the arrangement is configured to provide sample flow between the liquid chromatography separation column and the capillary electrophoresis separation device that is constant and without interruption.

2. The arrangement of claim 1, wherein the two-dimensional separation comprises the combination of nano-reversed phase liquid chromatography with a capillary zone electrophoresis.

3. The arrangement of claim 1, wherein the analyte mixture comprises peptides.

4. The arrangement of claim 1, wherein at least one further concentration zone is defined in a segment between a further series of electrodes in the area of the interface between the two devices.

5. The arrangement of claim 4, wherein the further concentration zone comprises a preconcentration zone or pre-preconcentration zone.

6. The arrangement of claim 1, characterised in that micro electrodes are arranged before insertion of the individual samples or sample fractions leaving the first device in the second device, the microelectrodes comprising micro channels in contact with a capillary channel connecting the first with the second device.

7. The arrangement of claim 6, wherein the micro electrodes are used for the preconcentration and/or pre-preconcentration of an analyte.

8. The arrangement of claim 6, wherein a very narrow aperture contacts the micro channels with a capillary channel connecting the first with the second device.

9. The arrangement of claim 6, wherein the micro-channels are filled with a polymer or other ion selective material.

10. The arrangement of claim 9, wherein the polymer comprises polytetrafluoroethylene with sulfonic acid groups interspersed therein.

11. The arrangement of claim 9, wherein the polymer has an affinity for water and protons.

12. A method for two-dimensional liquid chromatography/electrophoresis/mass spectrometry comprising separating a sample mixture in a reversed phase liquid chromatography followed by a capillary zone electrophoresis, wherein in the area of the interface between the reversed phase liquid chromatography and the capillary zone electrophoresis the fractions leaving the reversed phase liquid chromatography are concentrated before insertion into the following capillary zone electrophoresis, wherein the fractions leaving the reversed phase liquid chromatography are concentrated in at least one segment defined by two electrodes or a series of electrodes by applying a voltage across with polarity opposite to the charge of the components of the fraction sufficiently strong to apply a dragging force of the hydrodynamic flow and in that the insertion into the capillary zone electrophoresis is carried out by turning off the potential difference between the electrodes, wherein the flow of the sample between the liquid chromatography separation column and the capillary electrophoresis separation device is not interrupted.

13. The method of claim 12, wherein the fractions are concentrated on applying at least one electric field and in that the concentrated fractions are inserted into the following capillary zone electrophoresis in absence or reversion of at least one electric field.

14. The method of claim 12, wherein the individual components of the fraction separated by the capillary zone electrophoresis are sprayed into a mass spectrometer.

* * * * *